United States Patent [19]

Gammill

[11] Patent Number: 4,820,851
[45] Date of Patent: Apr. 11, 1989

[54] INTERMEDIATES FOR ANTIATHEROSCLEROTIC FUROCHROMONES

[75] Inventor: Ronald B. Gammill, Portage, Mich.

[73] Assignee: The Upjohn Company, Kalamazoo, Mich.

[21] Appl. No.: 885,365

[22] Filed: Jul. 14, 1986

Related U.S. Application Data

[62] Division of Ser. No. 603,533, Apr. 25, 1984, Pat. No. 4,614,809, which is a division of Ser. No. 378,686, May 17, 1982, Pat. No. 4,459,420.

[51] Int. Cl.$^4$ ........................................... C07D 307/86
[52] U.S. Cl. .................................... 549/462; 549/471
[58] Field of Search ................................ 549/462, 471

[56] References Cited

U.S. PATENT DOCUMENTS 2,680,119  6/1954  Robertson et al. ................. 549/471
4,284,569  8/1981  Gammill ............................. 549/471

OTHER PUBLICATIONS

Row et al., Indian J. Chem., 5, 105 (1967).

Primary Examiner—Nicky Chan
Attorney, Agent, or Firm—Martha A. Cox; Donald L. Corneglio

[57] ABSTRACT

The present invention particularly provides novel benzofuran compounds which are useful in the synthesis of khellin and antiatherosclerotic furochromones.

2 Claims, No Drawings

INTERMEDIATES FOR ANTIATHEROSCLEROTIC FUROCHROMONES

CROSS REFERENCE TO RELATED APPLICATIONS

This application is a division of application Ser. No. 603,533 filed Apr. 25, 1984, now issued as U.S. Pat. No. 4,614,809 on Sept. 30, 1986, which is a division of application Ser. No. 378,686, filed May 17, 1982, now issued as U.S. Pat. No. 4,459,420 on July 10, 1984.

BACKGROUND OF THE INVENTION

The present application relates to novel benzofuran compounds which are useful in the synthesis of khellin and antiatherosclerotic furochromones.

PRIOR ART

Methods of the total synthesis of khellin are known, as are certain chemical intermediates useful in its synthesis.

The use of pyrogallol in the synthesis of khellin intermediates is known. For example, the transformation of pyrogallol to the khellin intermediate 1-(2,3-dihydro-6,7-dihydroxy-5-benzofuranyl)ethanone is known. The parahydroxylation of this intermediate is also known. See Row, L. R., et al., Indian J. Chem., 5: 105 (1967) describing this transformation and the subsequent dimethylation to yield known khellin intermediates. U.S. Pat. No. 4,284,569 provides a variety of novel anti-atherosclerotic furochromones.

SUMMARY OF THE INVENTION

The present invention particularly provides:
(a) a benzofuran of formula III wherein $R_2$ is $C_1$–$C_4$ alkyl;
(b) a benzofuran of formula IV wherein $R_5$ is $C_2$–$C_4$ alkyl; and
(c) a benzofuran of formula V wherein one of $R_6$ and $R_7$ is $C_1$–$C_4$ alkyl and the other is $C_2$–$C_4$ alkyl with the proviso that $R_6$ and $R_7$ are different.

FORMULAS

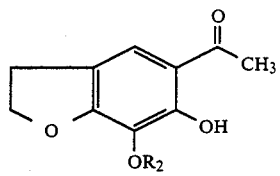

III

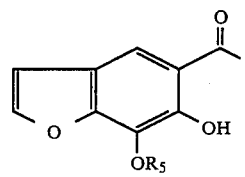

IV

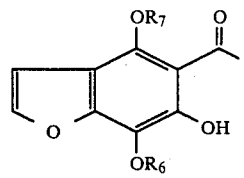

V

I claim:
1. A benzofuran of formula III:

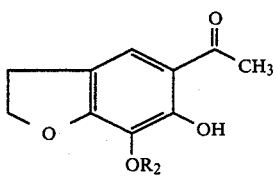

III wherein $R_2$ is $C_1$–$C_4$ alkyl.

2. A benzofuran of formula IV:

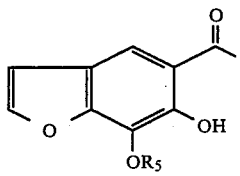

IV wherein $R_5$ is $C_2$–$C_4$ alkyl.

* * * * *